(12) United States Patent
Damadian et al.

(10) Patent No.: US 7,008,383 B1
(45) Date of Patent: Mar. 7, 2006

(54) METHOD OF CONDUCTING A NEEDLE BIOPSY PROCEDURE

(75) Inventors: Jevan Damadian, East Northport, NY (US); Jan Votruba, Brookhaven, NY (US); Mark Gelbien, Levittown, NY (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 10/728,376

(22) Filed: Dec. 4, 2003

Related U.S. Application Data

(63) Continuation of application No. 09/799,926, filed on Mar. 6, 2001, now Pat. No. 6,702,761.

(60) Provisional application No. 60/187,261, filed on Mar. 6, 2000.

(51) Int. Cl.
*A61B 5/00* (2006.01)

(52) U.S. Cl. .................... 600/567; 600/568; 600/576

(58) Field of Classification Search ............... 600/562, 600/564–568; 604/163, 158, 159
See application file for complete search history.

(56) References Cited

U.S. PATENT DOCUMENTS

| | | |
|---|---|---|
| 3,308,823 A | 3/1967 | Peterson |
| 3,902,495 A | 9/1975 | Weiss et al. |
| 3,990,452 A | 11/1976 | Murry et al. |
| 4,223,676 A | 9/1980 | Wuchinich et al. |
| 4,306,570 A | 12/1981 | Matthews |
| 4,504,264 A | 3/1985 | Kelman |
| 4,613,328 A | 9/1986 | Boyd |

(Continued)

OTHER PUBLICATIONS

Reading, Carl C., M.D., "Nonvascular Intervention: Percutaneous Biopsy of Neck Masses and Percutaneous Ablation of Parathyroid Glands," Current Practice Of Interventional Radiology, 1991, pp. 170-174, B.C. Decker Inc., Philadelphia, Saadoon Kadir, M.D. Editor.

(Continued)

*Primary Examiner*—Kevin Lee
(74) *Attorney, Agent, or Firm*—Brandon N. Sklar; Kaye Schoter, LLP

(57) ABSTRACT

A vibration assisted needle device is disclosed for use in medical procedures such as needle aspiration biopsies. Reciprocation of the needle, such as a biopsy needle, eases the advance of the needle through tissue, penetration of the site of interest and the collection of sample at a site of interest. The device comprises a housing defining a chamber, a needle support external to the chamber for supporting a needle and a mechanism in the chamber for causing reciprocatory motion of the needle support. The needle support is preferably external to the housing. A syringe support may be connected to the housing for supporting a syringe. The reciprocatory mechanism may comprise means for converting rotational motion into reciprocating motion, such as a bearing or a rotor with a circumferential, angled groove on its surface, coupled to the needle support. The bearing or the rotor may be driven by a rotational motor, preferably located outside of the housing, or by a hydraulically driven turbine within the housing. Alternatively, the reciprocatory mechanism means may comprise a stationary solenoid and a movable solenoid for being coupled to the needle. Preferably, a second stationary solenoid is provided and the moving solenoid is between the two stationary solenoids. Energization of the stationary solenoid or solenoids by an alternating current for example, and energization of the movable solenoid by a direct current, or vice versa, attracts and repulses the movable solenoid, causing reciprocation of the needle. Methods and systems using the vibration assisted needle device are also disclosed.

22 Claims, 11 Drawing Sheets

U.S. PATENT DOCUMENTS

| | | |
|---|---|---|
| 4,634,420 A | 1/1987 | Spinosa et al. |
| 4,671,292 A | 6/1987 | Matzuk |
| 4,698,058 A | 10/1987 | Greenfeld et al. |
| 4,735,604 A | 4/1988 | Watmough et al. |
| 4,747,820 A | 5/1988 | Hornlein et al. |
| 4,804,364 A | 2/1989 | Dieras et al. |
| 4,869,258 A | 9/1989 | Hetz |
| 4,944,308 A | 7/1990 | Akerfeldt |
| 4,953,558 A | 9/1990 | Akerfeldt |
| 5,084,009 A | 1/1992 | Makool |
| RE34,056 E | 9/1992 | Lindgren et al. |
| 5,188,118 A | 2/1993 | Terwilliger |
| 5,284,156 A | 2/1994 | Schramm et al. |
| 5,286,256 A | 2/1994 | Mackool |
| 5,329,927 A | 7/1994 | Gardineer et al. |
| 5,348,022 A | 9/1994 | Leigh et al. |
| 5,507,298 A | 4/1996 | Schramm et al. |
| 5,538,010 A | 7/1996 | Darr et al. |
| 5,647,851 A | 7/1997 | Pokras |
| 5,674,235 A | 10/1997 | Parisi |
| 5,688,235 A | 11/1997 | Sakurai et al. |
| 5,728,130 A | 3/1998 | Ishikawa et al. |
| 5,800,389 A * | 9/1998 | Burney et al. .......... 604/164.01 |
| 5,916,229 A * | 6/1999 | Evans ...................... 600/567 |
| 5,938,635 A * | 8/1999 | Kuhle ...................... 604/506 |
| 6,402,701 B1 * | 6/2002 | Kaplan et al. ............. 600/567 |

OTHER PUBLICATIONS

Monsein, LH, Williams, WL, "Fine needle biopsy without syringe aspiration," PubMed, Cardiovasc. Intervent Radiology, Jan.-Feb. 1993; 16(1): 11-3.

Kopicki, Maria T., M.D. and Haefner, Hope K., M.D., "Management of the Palpable Breast Mass," OBGYN.net, Women's Primary Health Grand Rounds at University of Michigan, Timothy R.B. Johnson, M.D. and Hope K. Haefner, M.D. Editors, Originally published in "The Female Patient," Sep. 1998, Quadrant Publishing.

Zvonimir Papic, Bozo Colak, Zdenko Skrabalo, "Fine Needle Aspiration Biopsy (FNAB) of the Testicles," Diabetologica Croatica, 28-3, 1999, Croatia.

Kinney, Thomas B., M.D., "Percutaneous Biopsy," Vascular and Interventional Radiology, 1999, pp. 379-391, W.B. Saunders Company, U.S.A., Karim Valji, M.D. Editor.

* cited by examiner

METHOD OF CONDUCTING A NEEDLE BIOPSY PROCEDURE

This application is a continuation of application Ser. No. 09/799,926, filed on Mar. 6, 2001, which issued on Mar. 9, 2004 bearing U.S. Pat. No. 6,702,761 B1, which claims the benefit of provisional appl. 60/187,261 filed on Mar. 6, 2000, is assigned to the assignee of the present invention and is incorporated by reference, herein.

FIELD OF THE INVENTION

A needle device, and more particularly, a biopsy needle device which is driven to vibrate in a direction along the axis of the needle to ease passage of the needle through tissue and the collection of a sample at a site of interest.

BACKGROUND OF THE INVENTION

When an abnormal area of tissue, such as a tumor, is discovered by non-invasive means, a tissue diagnosis is often required in order to determine the appropriate treatment. This requires that an adequate sample of tissue be removed from the patient for histopathological analysis. The tissue may be obtained in a variety of ways, such as surgical excision, fine needle aspiration biopsy or large needle core biopsy.

Fine needle aspiration biopsy, using needles with diameters of 20–22 Gauge, is minimally invasive. Typically, a biopsy needle with a stylet is inserted into the abnormal tissue, under the guidance of an imaging modality, such as ultrasound or magnetic resonance imaging ("MRI"). The stylet is then removed. A syringe is attached to the needle, suction is applied through the syringe and then the needle is manually thrust into and out of the tissue to capture and remove cellular material. However, rather than cutting the tissue to enable collection in the needle bore, the thin needle tends to displace the tissue, especially rigid malignant tissue. Therefore, only a small number of cells may be obtained. Even after repeated attempts, a sufficient amount of tissue might not be obtained. Displacement of tissue also alters the frame of reference defined by the imaging modality.

To improve yield, large bore needles, having diameters of 18–10 Gauge, have been used. However, the risk of damage to the tissues that the needle has to traverse to reach the area of pathology, as well as the risks of bleeding, infection and patient discomfort, rise with increasing needle thickness. Healing time may therefore be increased. Large needle core biopsy needles may also cause significant damage to certain organs, such as the lungs and the spleen. As with fine needles, displacement of movable tissues, such as breast tissue, is also a problem.

SUMMARY OF THE INVENTION

The problems encountered in the prior art are overcome in the devices, systems and methods of the present invention by reciprocating the biopsy needle along its longitudinal axis. Such reciprocation or vibration eases the advance of the needle through tissue to the site of interest, decreasing damage to the tissue. It is believed that the rapid movement of the needle decreases the friction between the needle and the surrounding tissue. The reciprocation of the needle also eases the penetration of the site of interest and the collection of tissue at the site of interest, with minimal displacement of the tissue, as the inertia of the tissue of the site of interest maintains the tissue essentially stationary as the tissue is penetrated by the rapidly moving needle. The present invention provides for greater tissue collection than that typically obtained by fine needle aspiration, without the risk of tissue damage and tissue displacement associated with the use of large bore needles. While fine needles are preferably used with the present invention, large bore needles may be used, as well.

DETAILED DESCRIPTION OF THE INVENTION

Figure 1:
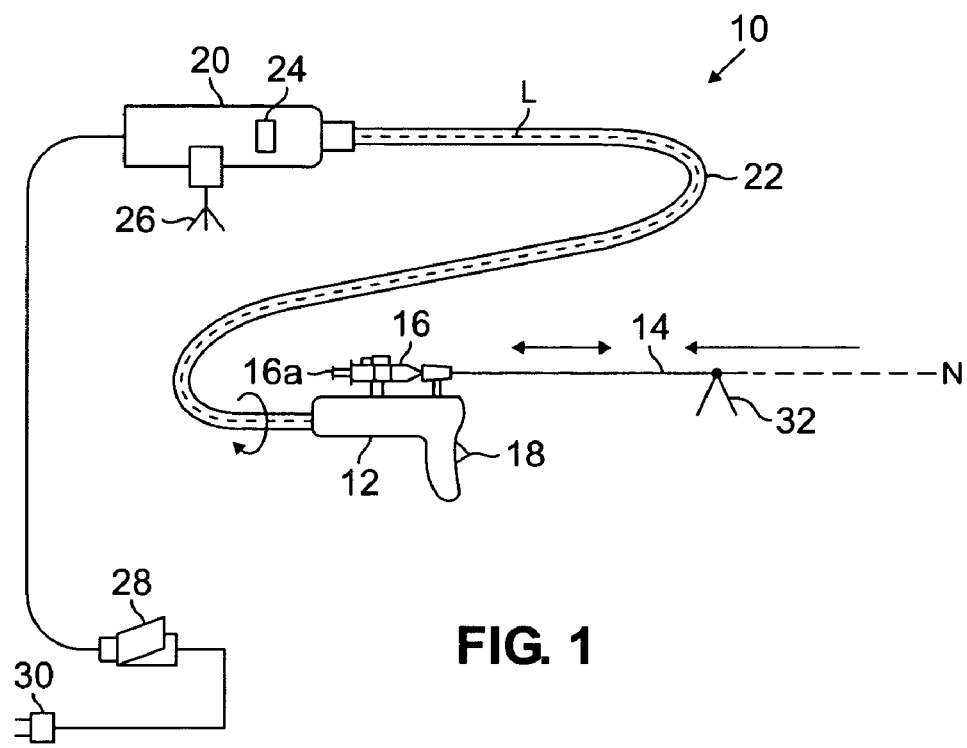
FIG. 1 shows a biopsy needle system in accordance with a preferred embodiment of the present invention, including a vibration assisted needle device.

FIG. 1 shows a biopsy needle system 10 in accordance with a preferred embodiment of the present invention. The system includes a vibration assisted needle device 11 including a needle 14 and a syringe 16. The syringe 16 includes a plunger 16*a*. Withdrawal of the plunger when the needle is at or within the target tissue provides suction for drawing tissue into the bore of the needle 14. The needle may be connected to a suction or vacuum pump, as well. The device 11 may include a trigger 18 for activating a drive mechanism for causing vibration of the needle 14.

In this embodiment of the invention, the drive mechanism is a rotating device, such as a drill 20. The drill 20 may be connected to the device 11 through a flexible shaft 22. Rotation of the drill 20 causes rotation of the shaft 22 about its longitudinal axis "L", shown in phantom extending through the center of the shaft 22 in FIG. 1, resulting in the reciprocation of the needle 14 along its longitudinal axis "N", as described further below. The drill 20 may include an on/off switch 24, which may also include a variable speed setting and a stand 26 for supporting the drill 20 on the floor or on a table (not shown). A foot switch 28 may also be provided for activating the drill 20. The drill 20 may include a plug 30 for connection to an ordinary outlet (110 volts) (not shown) or the drill 20 may be battery powered. A needle guide 32 may be provided to assist in supporting and guiding the needle 14.

Figure 2:
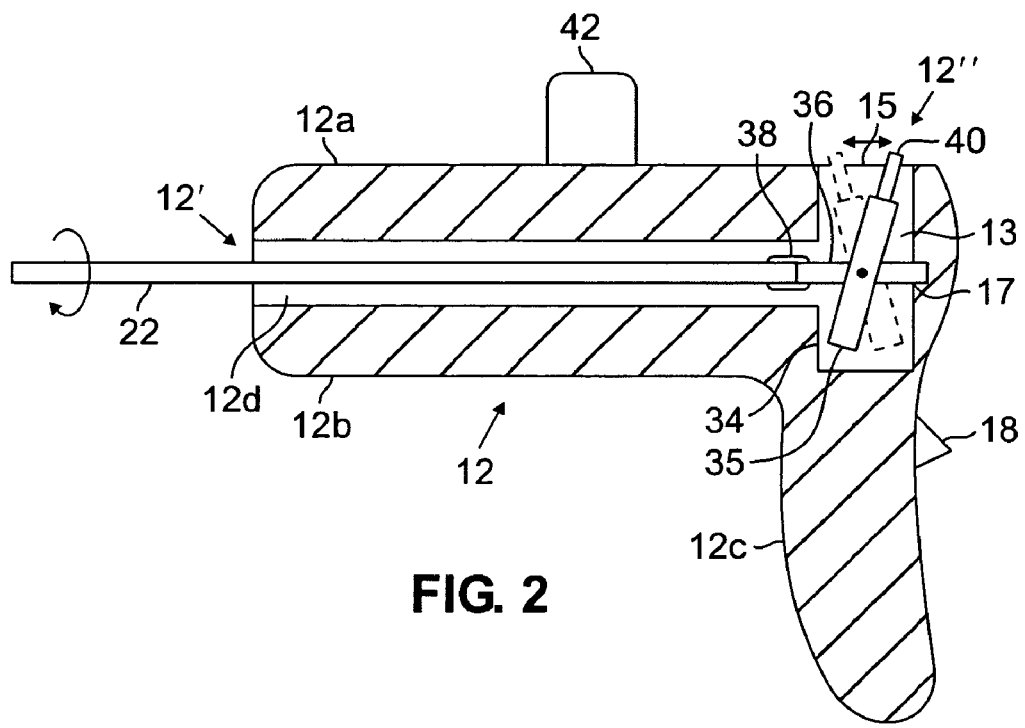
FIG. 2 is a cross-sectional view of the vibration assisted needle device of FIG. 1 in accordance with one embodiment of the present invention.

FIG. 2 is a cross-sectional view of the vibration assisted needle device 11, showing a housing 12 which may comprise a top portion 12*a* and a bottom portion 12*b* connected to each other by screws (not shown) or other appropriate means. In this embodiment, the bottom portion 12*b* includes a handle portion 12*c* including the trigger 18. A channel 12*d* is defined by the top portion 12*a* and the bottom portion 12*b* of the base 12, for receiving the shaft 22. The channel 12*d* extends from the rear end 12' of the housing 12 to a chamber 13, also defined by the top portion 12*a* and the bottom portion 12*b*, in the front portion 12" of the device 12. A ball bearing assembly 34 resides in the chamber 13, coupled to the shaft 22 and to the needle 14. The shaft 22 enters the channel 12*c* of the housing 12 through the rear end of the housing 12. A rod 36 extends from the ball bearing assembly 34 into the channel 12*c*. The shaft 22 and the rod 36 may be connected through a chuck 38, for example. The rod 36 preferably extends through the ball bearing assembly 34. The front of the rod 36 is supported by a shoulder 17 in the chamber 13. FIG. 2 also shows a clip 42 for supporting the syringe 16.

Figure 3:
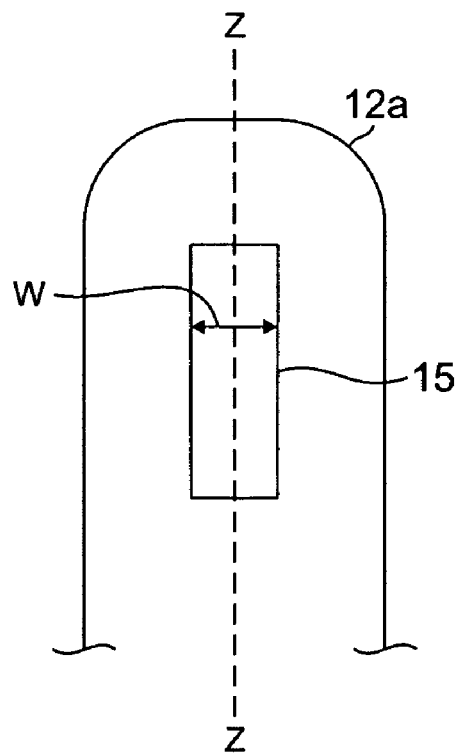
FIG. 3 is a top view of a front section of the needle device of FIG. 2, showing a slot in a housing of the device.

A post 40 extends from the top of the ball bearing assembly 34, out the top of the top portion 12*a* of the housing 12, through a longitudinal slot 15 in a wall of the housing. The slot 15 has a longitudinal axis "Z", preferably aligned with the axis of the rod 36 (see FIG. 5*a*) and to the longitudinal axis of the needle 14 supported by the needle support 60. FIG. 3 is a top view of the front section of the top portion 12*a*, showing the slot 15. The post 40 is not shown in FIG. 3. The post 40 is connected to a needle support 60, discussed below with respect to FIG. 6.

In accordance with one aspect of the present invention, the needle support 60 is external to the housing 12 so that the needle 14 is supported external to the housing. The syringe support is then also external to the housing. This facilitates removal of the needle 14 and syringe 16 after a procedure and enables the use of a disposable syringe 16. Alternatively, the needle support 60 could extend through a slot in an interior wall of the housing 12 into another chamber of the housing. The syringe 16 would then also reside in a chamber of the housing and an opening would be provided for the needle to exit the housing.

Figure 4:
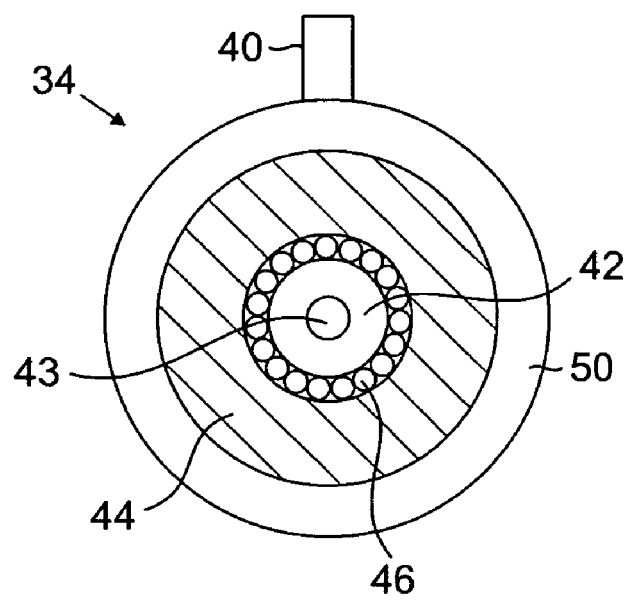
FIG. 4 is a front view of a ball bearing assembly for causing reciprocation of the needle in the embodiment of FIG. 2.

FIG. 4 is a front view of the ball bearing assembly 34. The assembly comprises a rotatable inner disk 42 and an outer disk 44. The rotatable inner disk 42 includes a hole 43 for receiving the rod 36. The rod 36 preferably has a diameter slightly larger than the diameter of the hole 43, so that the rod 36 is tightly engaged. Ball bearings 46 are provided between the rotatable inner disk 42 and the outer disk 44. An annular ring 50 is provided around the outer disk 44. The annular ring 50, which may be a plastic or fiberglass, for example, includes the tab 40. A suitable fiberglass is G-10, available from AIN Plastics, Mount Vernon, N.Y., for example. The inner diameter of the annular ring 50 is preferably slightly less than the outer diameter of the outer disk 44, so that the outer disk 44 fits tightly within the annular ring 50. The inner and outer disks 42, 44, and the ball bearings 46, may be metal or metal alloy. Preferably, the metal or metal alloy are non-ferromagnetic, such as stainless steel or titanium. The ball bearing assembly 34 may be non-metallic, such as plastic, as well. Instead of using ball bearings 46, low friction surfaces may be provided between the inner and outer disks 42, 44.

Figure 5A:
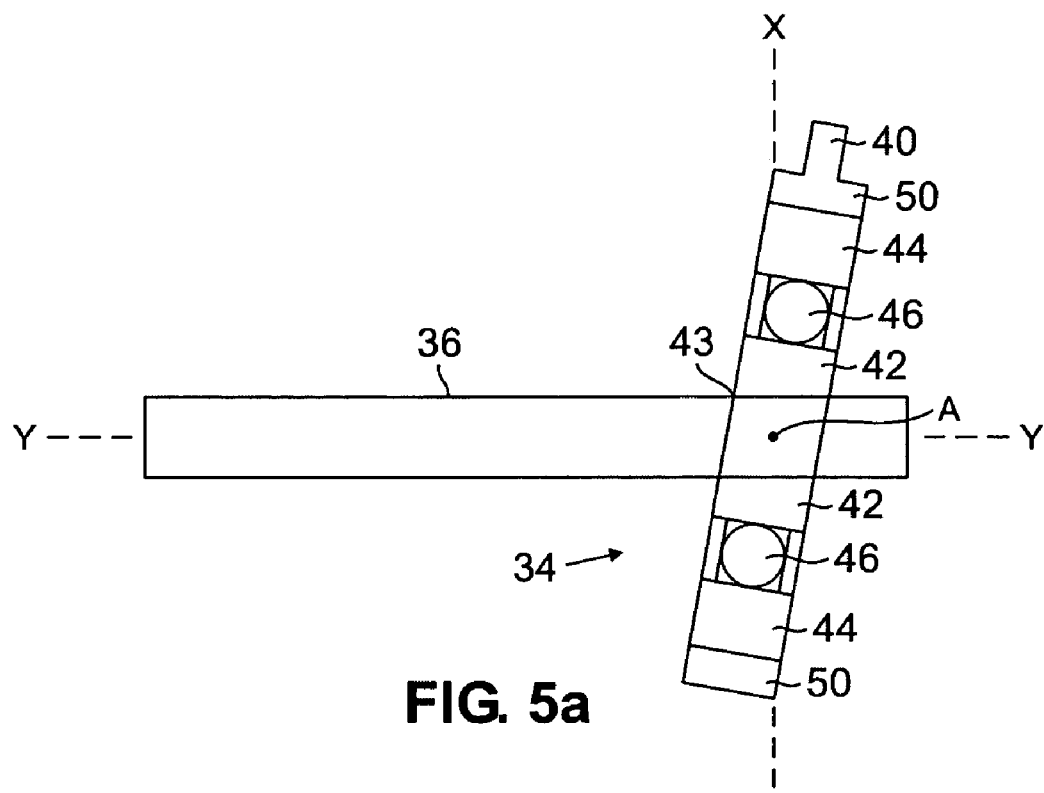
FIG. 5a and FIG. 5b are cross-sectional views of the ball bearing assembly of FIG. 4, and a rod for coupling the ball bearing assembly to a source of rotational motion, such as a motor.
Figure 5B:
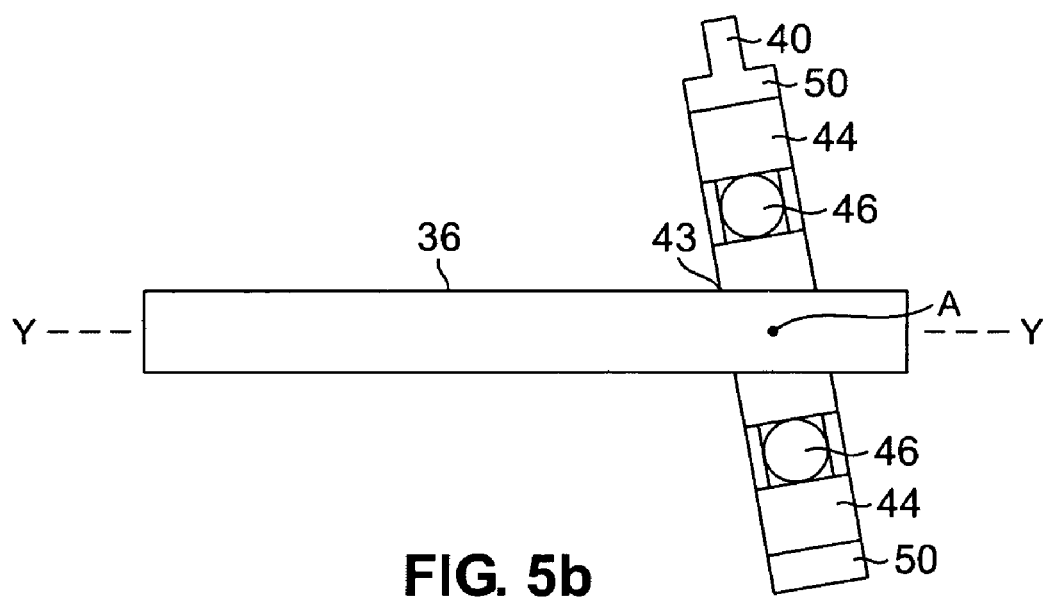

FIG. 5*a* and FIG. 5*b* are cross-sectional views of the ball bearing assembly 34 and the rod 36. The rod 36 and the hole 43 for receiving the rod 36 lie along an axis "Y". The axis through the hole 43 is at an oblique angle with respect to a plane containing the ball bearing assembly 34. The ball bearing assembly 34 is therefore angled with respect to an axis "X" (shown exaggerated in FIG. 5*a*) perpendicular to the axis "Y". Alternatively, the surface of the rod 36 may be angled to provide for the oblique mounting of the ball bearing 34. Rotation of the rod 36 by the shaft 22 causes rotation of the inner disk 42. Since the post 40 extends through the slot 15 in the top of the base 12, which provides only one degree of freedom of movement for the post 40 (along the longitudinal axis Z of the slot 15), the outer disk 44 cannot rotate about the axis of the rod 36. Rotation of the inner disk 42 therefore provides a resultant force on the post 40 along the axis of the longitudinal slot, causing rotation of the outer disk 44 and the post 40 about an axis "A" perpendicular to the rod 36 and to the axis Z. The post 40 thereby reciprocates forward and backward along the axis Z of the slot 15, as the inner disk 42 is rotated. FIG. 5*b* shows the position of the ball bearing assembly 34 upon one-half rotation of the rod 36. Upon a complete rotation, the ball bearing assembly 34 returns to its original position, shown in FIG. 5*a*. The angle of the hole 43 with respect to the plane of the bearing assembly 34 and the resulting angle of the bearing assembly with respect to the rod 36 are dependent on the desired distance of travel of the needle 14 and the distance from the center of the bearing 34 to the center of the needle 14, as discussed further, below. An angle of from about 0.5 to about 6 degrees is believed to be suitable.

The slot is preferably just slightly wider than the width "W" of the post 40, to restrict the lateral motion of the post, and hence the needle support 60 and the needle 14. For example, the width "W" of the slot may be 0.17 inches and the width of the post may be 0.11 inches.

Figure 6:
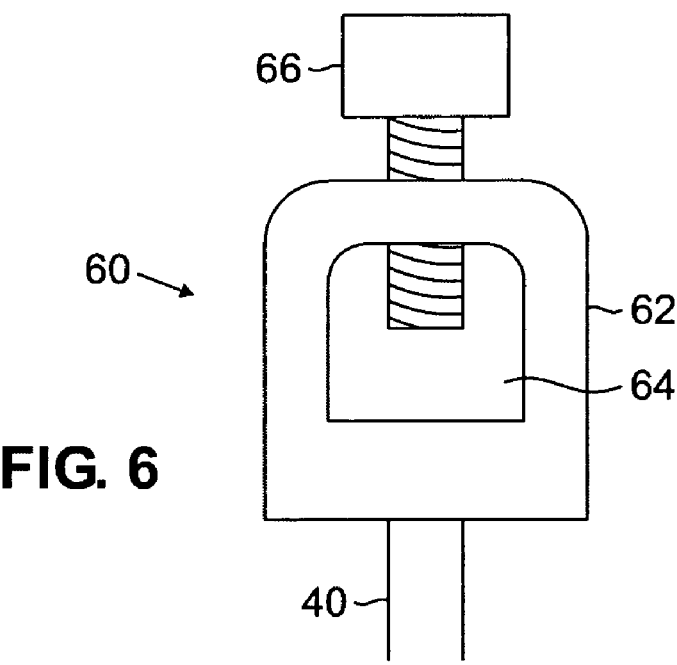
FIG. 6 is a front view of a needle support, in the vibration assisted needle device of FIG. 2.
Figure 7:
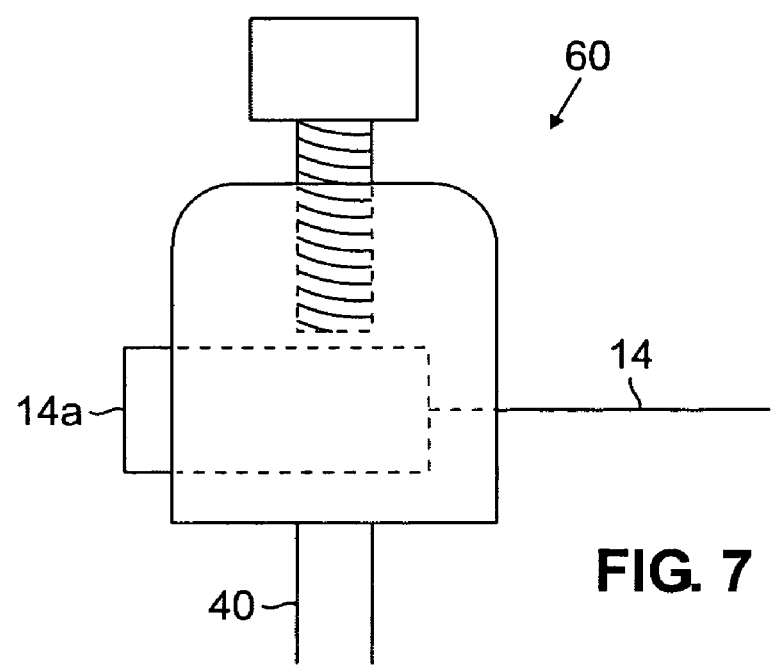
FIG. 7 is a side view of the needle support of FIG. 6, with a base of a needle secured thereto.

FIG. 6 is a front view of a needle support 60, connected to the post 40. The needle support 60 comprises a base 62 with a central opening 64 for receiving the rear end of the needle 14. The rear end 14*a* of the needle 14 is typically a rectangular base. A screw 66 is provided to bear against the base 14*a* of the needle 14, securing the needle 14 to the base 62. Reciprocation of the post 40 causes reciprocation of the needle support 60 and the needle 14 secured thereto. FIG. 7 is a side view of the needle support 60 of FIG. 6, with the base 14*a* of the needle 14 secured thereto.

The dimensions of the ball bearing assembly 34, the post 40 and the needle support 60, and the angle of the ball bearing assembly 34, are adjusted so that the needle 14 moves the desired distance during reciprocation. A distance from about 1 to about 3 mm from the rear most position of the tip of the needle 14 to the forward most position of the needle is preferred. For example, for the needle 14 to move a distance of about 2 mm, the distance from the center of the ball bearing assembly 34 to the center of the base 14a of the needle 14 may be about 45 mm and the ball bearing assembly 34 may be mounted at an angle of about 1.25° with respect to the rod 36.

Figure 8:
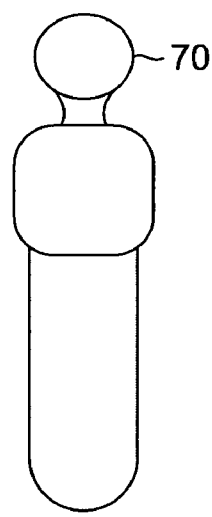
FIG. 8 is a rear view of the needle device of FIG. 2, showing a syringe support.
Figure 9:
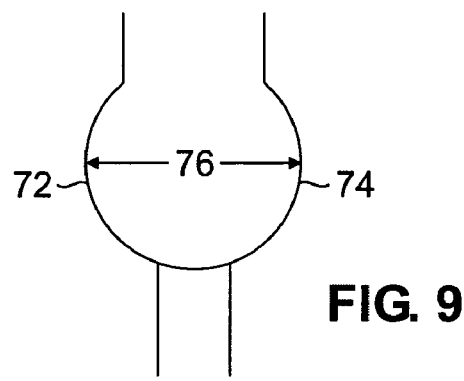
FIG. 9 is a view of an alternative syringe support.

FIG. 8 shows a rear view of the housing 12, showing the syringe support 42. In the embodiment of FIG. 8, the syringe support 42 is a ring 70 with an inner diameter slightly larger than the outer diameter of the syringe 16. This enables the syringe 16 to reciprocate as the needle 14 is reciprocated. Alternatively, the syringe support 42 may be a clip 72, as shown in FIG. 9. The clip 72 has flexible arms 74 defining a bulbous receiving region 76 with an inner diameter slightly larger than the outer diameter of the syringe, as well.

Figure 10:
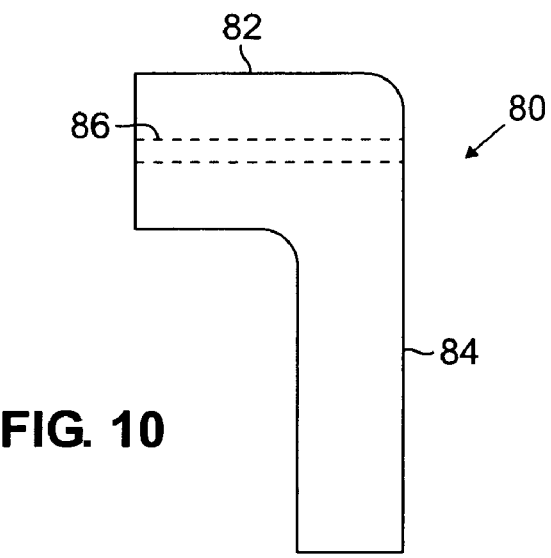
FIG. 10 is a side view of an example of a needle guide.

As mentioned above, a needle guide 32 may be used to support the shaft of the needle 14 during a procedure. FIG. 10 is a side view of an example of a needle guide 80. The needle guide 80 may be an L-shaped piece of material with a short arm 82 and a long arm 84. The material may be a polymeric material such as polyethylene, for example. A hole 86, shown in phantom in FIG. 10, extends through the short arm 82 for receiving the needle 14. A doctor or other person assisting in the procedure may grip the long arm of the needle guide 32, to stabilize and guide the needle 14 extending through the hole 86. The housing 12 may also be supported by a stereotactic device for precise positioning of the needle 12.

The rotational motor 20 is preferably capable of rotating from about 20,000 rotations per minute (333 rotations per second) to about 60,000 rotations per minute. Since the ball bearing assembly 34 returns to its original position upon a complete rotation of the motor, the needle 14 reciprocates at the speed of the motor. A Dremel® Multipro™ Motor available from Dremel®, Racine, Wis., may be used, for example. The motor 20 is preferably provided external to the device 11, to minimize the weight of the device. In addition, external placement of the motor 20 facilitates use of the device 11 in an MRI guided procedure, since the motor 20 can be placed in a location where it will not interfere with the MRI system, as discussed further, below. The motor 20 could, however, be contained within the device 11, if desired. A plunger type motor capable of driving the needle 14 along its axis may be provided within the device and be coupled to a needle support 60 external to the device 11, as well.

Operation of the vibration assisted needle device 10 of FIGS. 1–10 will now be described. The needle 14 is inserted into the needle support 60 and engaged by rotation of the screw 66 onto the wide base 14a of the needle 14. A stylet (not shown) is typically provided through the bore of the needle 14. The syringe 16 is not typically connected to the needle 14 or supported by the syringe support 42 at this time. The reciprocatory motion of the needle 14 is preferably started prior to insertion of the needle 14 into the patient, by engaging the trigger switch 18, the foot switch 28 or the switch 24 on the motor 20. The rotation of the motor 20 causes rotation of the shaft 22 about its longitudinal axis, which causes reciprocation of the ball bearing assembly 34 and the needle 14. The doctor, who is holding the device 11 by its handle 12c, inserts the needle 14 into the patient by advancing the device 11. The tissue of interest is approached, typically, under the guidance of an imaging modality, such as MRI. The shaft of the needle 14 may be stabilized by the needle guide 34 during the insertion and advance of the needle 14 to the tissue of interest.

Reciprocation of the needle 14 may be stopped when the needle 14 is proximate the tissue of interest or after the site of the tissue of interest is penetrated. Preferably, the tissue of interest, which may be a tumor, for example, is penetrated while the needle is reciprocating. The stylet is removed and the syringe 16 is inserted into the syringe support 42 and attached to the base 14a of the needle 14. The plunger 16a is then withdrawn to create negative pressure in the syringe 16 and in the bore of the needle 14. Reciprocation of the needle 14 is started again, to penetrate the tissue of interest, if necessary, and to collect tissue at the site of interest. The device 11 may be moved slightly forward and backward by the doctor, along the longitudinal axis N of the needle 14, to further cause the needle 14 to cut the tissue of interest. The cut tissue is drawn into the bore of the needle 14 due to the negative pressure created by the withdrawn plunger 16a. Alternatively, the rear end of the syringe or the needle 14 may be connected to the pump to draw the cut tissue into the needle shaft.

After a sufficient amount of tissue has been collected, the needle 14 is withdrawn from the patient. The excised tissue may be removed from the bore of the needle 14 by insertion of the plunger 16a into the syringe or insertion of the stylet into the bore of the needle 14.

The reciprocatory motion of the needle 14 assists in the passage of the needle 14 through body tissue to the site of interest, decreasing tissue damage and recovery time for the patient. It is believed that the friction between the needle and the surrounding tissue is decreased due to the reciprocatory motion. The reciprocatory motion also assists in the penetration of the tissue of interest, such as a tumor, with minimal displacement of the tissue of interest. The inertia of the tissue of interest maintains the tissue essentially stationary with respect to the rapidly reciprocating needle 14, enabling the needle 14 to penetrate the tissue. Reciprocation also improves tissue collection by fine biopsy needles (20–22 Gauge), obviating the need for the use of large bore needles (18–10 Gauge). However, while the use of large bore needles is not preferred because of the potential for increased tissue damage, large bore needles may be used with the devices, systems and methods of the present invention.

Since the reciprocating portions of the device 11, needle 14 and the needle support 60 move rapidly and have very low mass (preferably about $\frac{1}{100}$ or less of the mass of the housing 12 and the other components within the housing), the needle's momentum does not cause appreciable recoil.

As discussed above, the needle 14 may be advanced to the site of interest under the guidance of MRI. The embodiment of FIGS. 1–10 can be made entirely of non-ferromagnetic material, which will not yield an MRI signal and will not interact with the magnetic field of the MRI system. For example, the housing 12 may be made of brass or polyvinylchloride (PVC). This embodiment is therefore preferred for use in an MRI guided procedure. The drill 20 may be placed sufficiently far from the magnet of the MRI system so that it will not interfere with the magnet field generated by the magnet. The drill 20 may also be placed outside of the MRI room. The flexible shaft 22 can extend through an opening in a wall of the room, from the drill 20 to the support 12. Non-ferromagnetic needles for use with MRI are commercially available. For example, MRI-Compatible Lufkin® Aspiration Needles and MRI-Compatible Histology Biopsy Needles are available from EZEM®, Westbury, N.Y.

Figure 11:
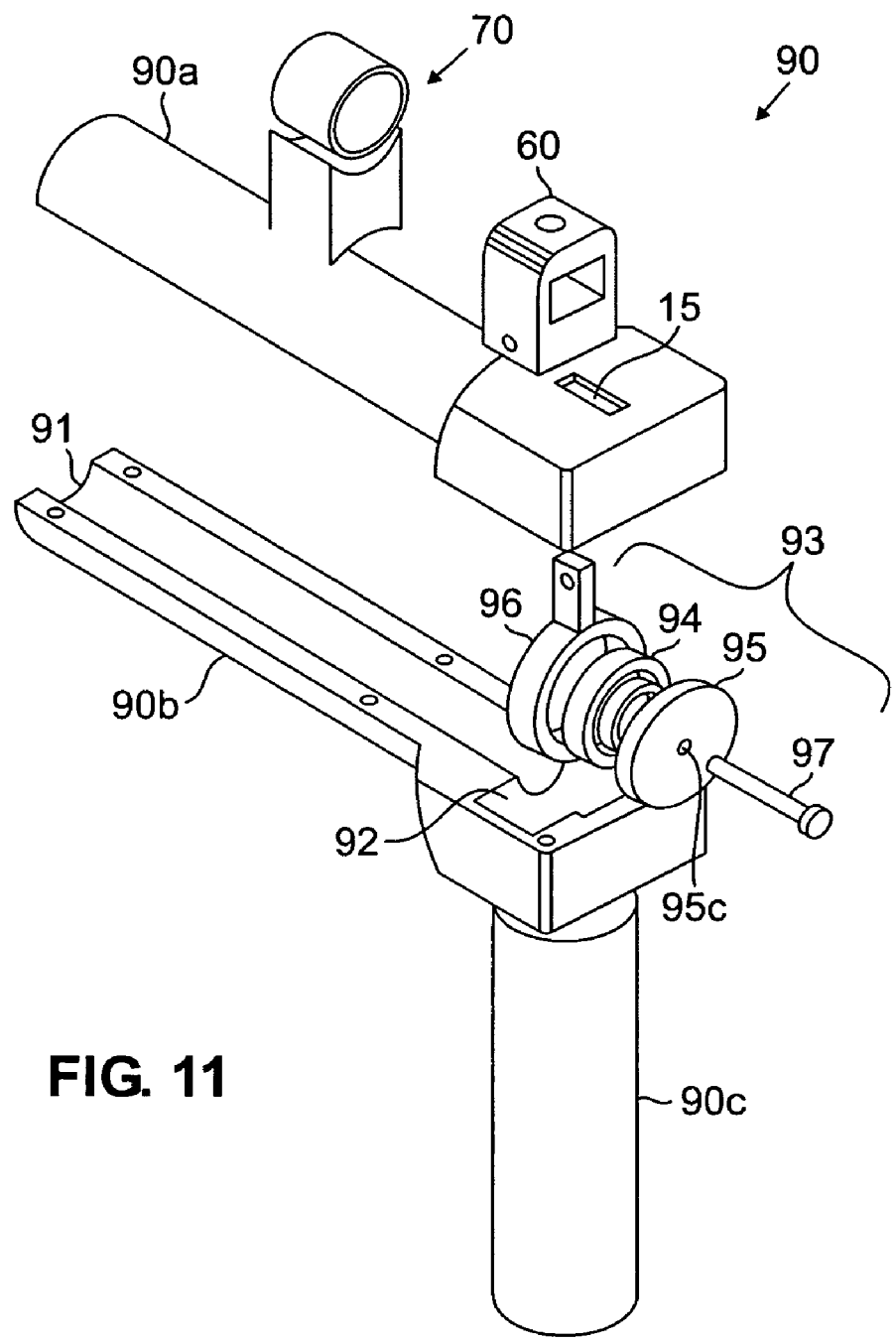
FIG. 11 is an exploded view of a preferred configuration of a vibration assisted needle device in accordance with the embodiment of FIG. 2.

FIG. 11 is an exploded view of a preferred configuration of a vibration assisted biopsy needle device 90 comprising a top housing 90a, a bottom housing 90b and a handle 90c. A groove 91 is shown in the bottom housing 90b. A corresponding groove (not shown) is provided in the top housing 90a. When the top and bottom housing 90a, 90b are mated, the grooves form a channel, such as channel 12c in FIG. 2, for receiving the shaft 22.

The bottom housing 90b also defines a chamber 92 for housing a ball bearing assembly 93. The top housing 90a defines a corresponding chamber (not shown), as well. In this embodiment, the ball bearing assembly 93 comprises a bearing 94, a cam 95 and a cam sleeve 96.

Figure 12:
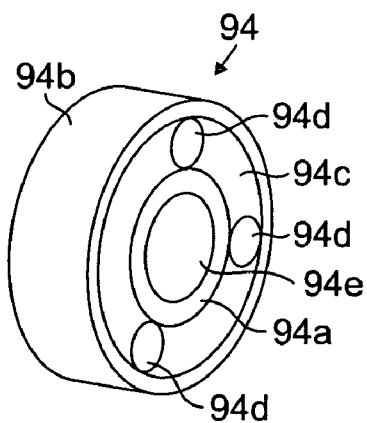
FIG. 12 is a perspective view of a bearing for driving the needle support in the configuration of FIG. 11.

FIG. 12 is a perspective view of the bearing 94, including an inner cylinder 94a, an outer cylinder 94b and a space 94c defined between the inner and outer cylinders. Ball bearings 94d are provided in the space 94c. While three ball bearings 94d are shown in FIG. 12, enough ball bearings to fill the space 94c are preferably provided. The inner cylinder 94a defines an opening 94e for receiving the cam 95.

Figure 13:
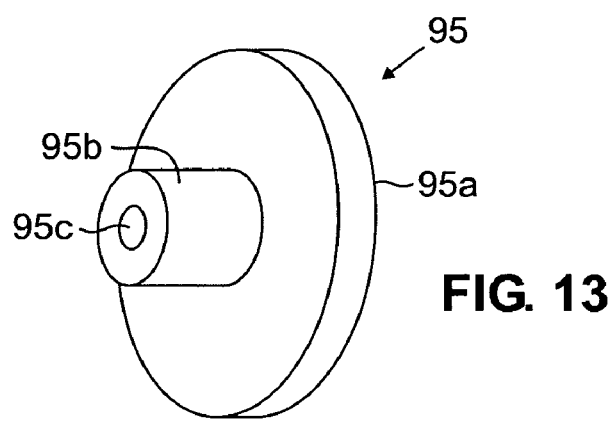
FIG. 13 is a perspective view of a cam for use with the bearing of FIG. 12.

FIG. 13 is a perspective view of the cam 95, including a disk 95a and a cylinder 95b. The cylinder 95b is to be inserted into the opening 94e in the bearing 94. (See FIG. 12). The outer diameter of the cylinder 95b is preferably slightly larger than the inner diameter of the opening 94e in the bearing of FIG. 12, so that the cylinder 95b fits tightly within the opening 94e. An opening 95c is defined through the cylinder 95b and the disk 95a. The opening 95c is angled with respect to the disk 95a. In this configuration, the angle of the opening 95c with respect to an axis perpendicular to the disk 95a, is about 1.15 degrees.

Figure 14:
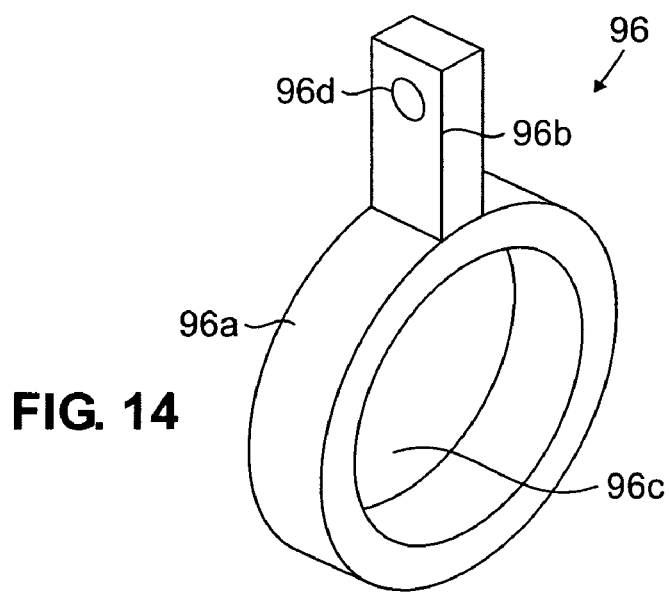
FIG. 14 is a perspective view of a cam sleeve for use with the bearing and cam of FIG. 12 and FIG. 13.

FIG. 14 is a perspective view of the cam sleeve 96. The cam sleeve 96 has a cylindrical body portion 96a and a post 96b protruding from the body portion 96a. The post 96b includes an opening 96d for attachment to the needle support. The cam sleeve 96 defines an opening 96c for receiving the bearing 94. As discussed above with respect to the annular ring 50, the cam sleeve 96 may be a plastic or fiberglass. The opening 96c preferably has an inner diameter slightly less than the outer diameter of the outer cylinder 94b of the bearing 94, so that the bearing 94 fits tightly within the cam sleeve 96.

Figure 15:
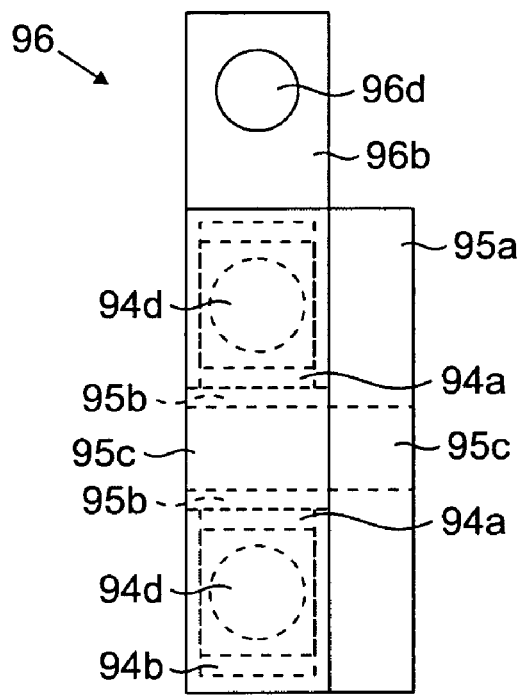
FIG. 15 is a side view of an assembly including the bearing, cam and cam sleeve of FIGS. 12, 13 and 14, respectively.

FIG. 15 is a view of the bearing assembly, showing the bearing 94 within the sleeve 96 and the cam 95 adjacent to the sleeve and bearing.

A rod 97 is provided through the opening 95c of the cam 95. One end of the rod 97 rests on a shoulder and the other end is connected to the shaft 22 through a chuck (not shown), as discussed above with respect to FIG. 2. When the rod 97 is received within the opening 95c, the angle between an axis perpendicular to the rod 97 and the bearing 94, is about 1.15 degrees.

The tab 96b extends through the slot 15 in the top portion 90a, for connection to the needle support 60. The needle support device 60 is described above with respect to FIG. 6. The syringe holder 70, described above with respect to FIG. 8, is also shown. In this configuration, the needle reciprocates about 1.4 mm in each direction. With an angle of about 1.15 degrees, the distance from the center of the bearing to the center of the base of the needle is about 35.6 mm.

Figure 16:
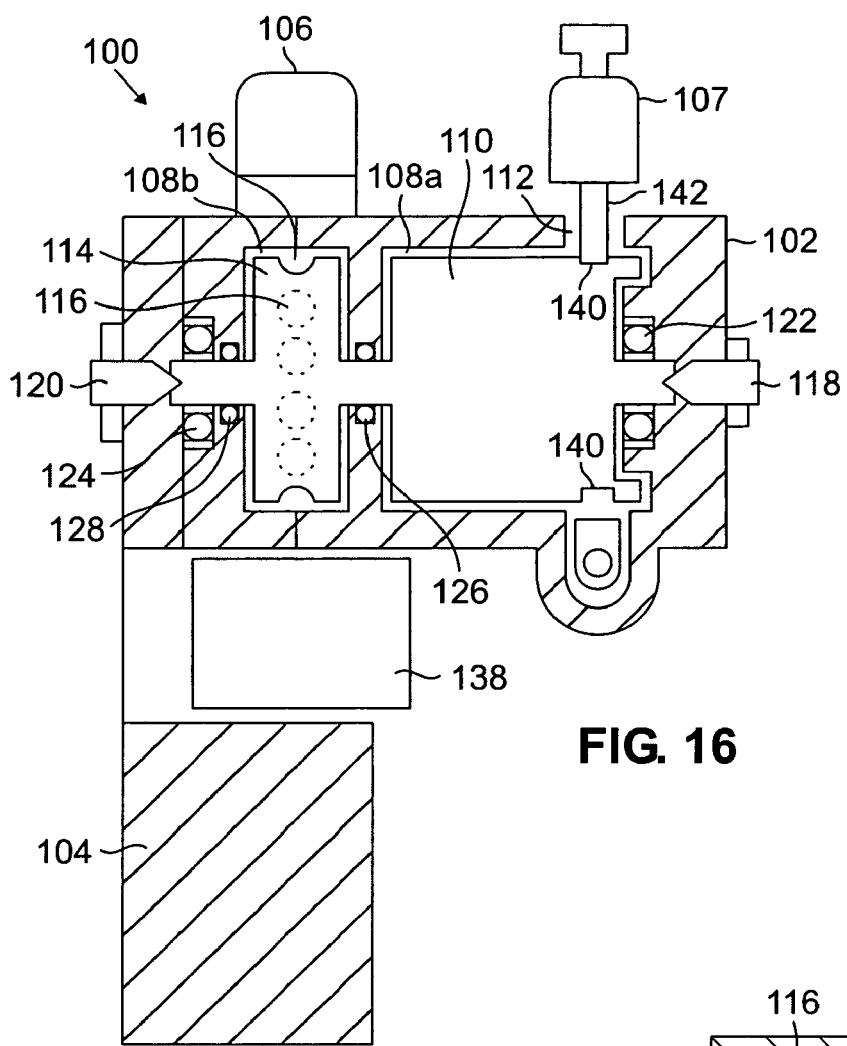
FIG. 16 is a cross-sectional view of a vibration assisted needle device in accordance with a second embodiment of the invention, wherein the needle support and the needle are driven hydraulically.
Figure 17:
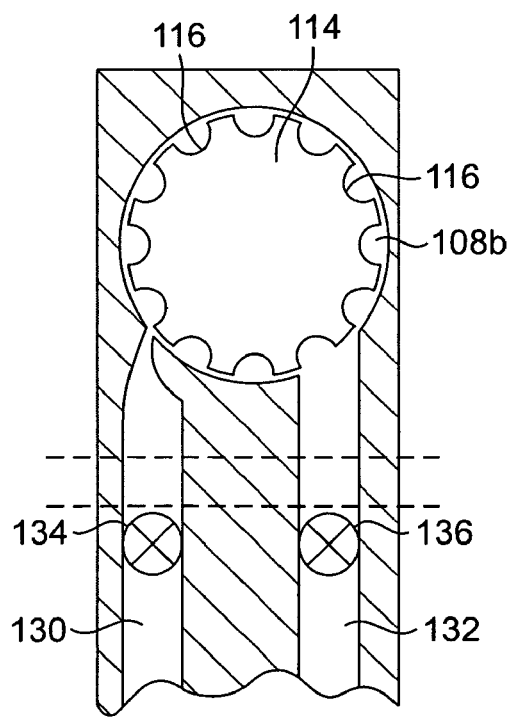
FIG. 17 is a partial cross-sectional view of the needle device of FIG. 15.

FIG. 16 is a cross-sectional view of a vibration assisted biopsy needle device 100 in accordance with another embodiment of the present invention, wherein reciprocation of the needle 14 is driven by an air or water pump. Air is preferred. The device 100 includes a housing 102 and a handle 104 depending from the housing 102. A syringe support 106 is mounted on the top of the housing 102. A needle support 107 is supported above the housing 102. The syringe support 106 and the needle support 107 may be the same as those discussed above with respect to the first embodiment. While the needle 14 and the syringe 16 are not shown in this view, the needle 14 and syringe 16 would be supported by the needle support 107 and the syringe support 106, and operated in the same manner as described above.

The housing 102 defines a cavity 108 with a first cavity portion 108a containing a rotor 110. A slot 112 through the housing 102 to the first cavity portion 108a is provided at the top of the housing 102. The top view of the slot 112 is the same as the top view of the slot 15 in FIG. 3. The housing 102 also defines a second cavity portion 108b of the cavity 108 containing a turbine 114. The turbine 114 is connected to the rotor 110 such that rotation of the turbine 114 causes rotation of the rotor 110. The turbine 114 has a plurality of notches 116 on its surface. The rotor 110 and the turbine 114 may be one integral device or a single cylinder.

A needle bearing 118 supported by the housing 102 bears against a forward side of the rotor 110. Another needle bearing 120 supported by an opposing side of the base 102 bears against a rear side of the turbine 114. The needle bearings 118, 120 prevent lateral motion of the rotor 110 and the turbine 114 with respect to the base 102. Point bearings could be used, as well. Ball bearings 122, 124 facilitate the low friction rotation of the rotor 110 and the turbine 114, with respect to the base 102. O-ring gaskets 126, 128 seal the second cavity 108b.

FIG. 16 is a partial cross-sectional view of the housing 102 and the turbine 114. A first passage 130 provides air or other fluid to the first cavity portion 108a to drive the turbine 114. A second passage 132 provides an outlet for the fluid from the first cavity portion 108a. Preferably, the fluid is removed from the first cavity portion 108a under pressure. Valves 134, 136 may be provided along the passages 130, 132, respectively.

Returning to FIG. 15, a switch 138 is provided on the handle 104, enabling control of the turbine 114 by an operator's finger. The switch 138 is connected to the valves 134, 136 in the flow passages 130, 132 in a conventional manner (not shown).

Figure 18:
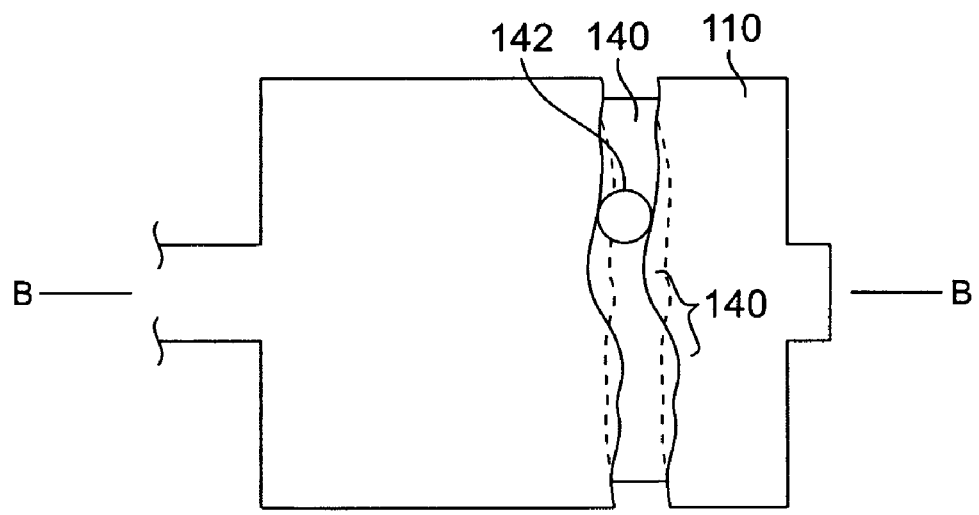
FIG. 18 is a top view of a portion of a groove on a rotor in the needle device of FIG. 16.

A circumferential, preferably continuous groove 140 is provided in the surface of the rotor 110, as shown in FIGS. 16 and 18. FIG. 18 is a top view of the rotor 110 and the groove 140. A first end of a shaft 142 is connected to a needle support 107 at the front end of the base 102. A second end of the shaft 142 is received within the groove 140. The groove 140 has a short, first portion 140a at a first oblique angle with respect to a rotational axis B—B of the rotor 110, as shown in FIG. 18. The remaining portion of the groove 140, shown partially in phantom, is at a second oblique angle smaller than the first angle with respect to the rotational axis. Preferably, the first angle is about twice as large as the second angle. In a preferred configuration, the first angle is about 2 to about 3 degrees and the second angle is about 1 to about 1.5 degrees. The length of the short, first portion 140a is preferably about one-third (⅓) of the circumference of the rotor 110. The length of the remaining portion of the groove 140 is about two-thirds (⅔) of the circumference of the groove 140.

The slot 112 has a longitudinal axis preferably parallel to and aligned with the axis B—B, and also at an oblique angle with respect to the portions of the groove 140. As above, the width "W" of the slot is preferably just slightly wider than the width of the shaft 142, so that the motion of the shaft is substantially limited to the longitudinal axis of the slot 112. Therefore, as the rotor 110 is turned, rotation of the groove 140 produces a resultant force on shaft 142 causing movement of the shaft 142 forward and backward along the longitudinal axis of the slot. If the longitudinal axis of the slot 112 is parallel to and aligned with the rotational axis B—B of the cylinder, then the angled portions of the groove 140 will cause a maximum reciprocation of the shaft 142, the needle support 107, and the needle. The groove 140 is positioned on the rotor 112 such that the shaft 142 is rapidly moved forward in the short portion 140a and is slowly moved backward in the remaining portion of the groove 140. Movement of the shaft 142 causes corresponding movement of the needle support 107 and the needle 14.

The reciprocatory motion of the needle 14 is started by engaging the switch 138, which opens the valves 134, 136 in passages 130, 132 respectively. Air or other such fluid is forced through the passage 134 into the cavity 108a. The fluid impinges on the notches 116 of the turbine 114, causing rotation of the rotor 110, and then exits the cavity 108b through the passage 132. As the rotor 110 rotates, the portion of the groove 140 received in the shaft 142 advances repeatedly through the short portion 140a and then the remaining portion of the groove 140, forcing the shaft 142 and the needle 14 forward and backward, respectively. Preferably, the needle 14 advances forward about 1–3 mm.

Preferably, while the needle is being reciprocated, it is inserted into the patient and advanced to the tissue of interest. As discussed above, reciprocation may be stopped when the needle is proximate the tissue of interest or after penetration of the tissue of interest. The switch 138 is then released, closing the valves 134, 136. Fluid flow through the cavity 108a ceases, rotation of the rotor 110 and the turbine 114 cease and the needle 14 stops moving. The stylet is removed and the syringe 16 is attached to the needle. The plunger 16a of the syringe 16 is withdrawn to create negative pressure in the syringe and the bore of the needle 14, as discussed above with respect to the first embodiment. Preferably, the switch 138 is then engaged to cause reciprocation of the needle 14 during penetration of the tissue of interest, if reciprocation was stopped prior to penetration, and collection of the tissue of interest. The device 100 may also be advanced by the doctor during the tissue collection to further cut and collect tissue at the site of interest within the bore of the needle 14. Suction in the bore of the needle 14 may also be provided through a pump connected to the rear end of the syringe, or to the needle 14.

Because of the inertia of the tissue of the site of interest, the tissue remains sufficiently stationary for the rapidly forwardly moving needle to more effectively penetrate, cut and collect tissue than non-reciprocating needles. The yield of fine biopsy needles is thereby improved. A slower speed of return of the needle is advantageous because it is less likely that collected tissue will escape from the needle bore, also improving yield. Large bore biopsy needles, while not preferred, may also be used in the present invention.

The needle support 107 (and the needle) may be driven forward and backward at a rate of from about 333 Hertz to about 1 Kilohertz. Only the needle, the needle support 107 and the post 142 move laterally. As above, the total mass of these components is much less (preferably about 1/100 or less) than the total mass of the device 100, to minimize recoil during movement of the needle.

The rotor 110 may be driven by a flexible shaft connected to a rotational motor, as in the first embodiment, as well.

The turbine 114 and the rotor 110 are preferably integrally formed of stainless steel or brass, for example. The turbine 114 and rotor 110 may also be two separate parts, connected together. It is preferred to provide a distinct rotor portion 110 and a distinct turbine 114 portion in distinct cavity portions 108a, 108b because it is easier to seal the cavity 108b. However, a single cylinder with a forward portion including the circumferential groove 140 and a rear portion including notches 116, may be provided in the cavity to act as both the rotor and the turbine. The portion of the cavity 108 containing the turbine would then need to be sealed.

The turbine 114 may also be used to drive the ball bearing assembly 34 of the first embodiment and the rotor of the second embodiment may be driven by a rotational motor, as in the first embodiment.

Figure 19:
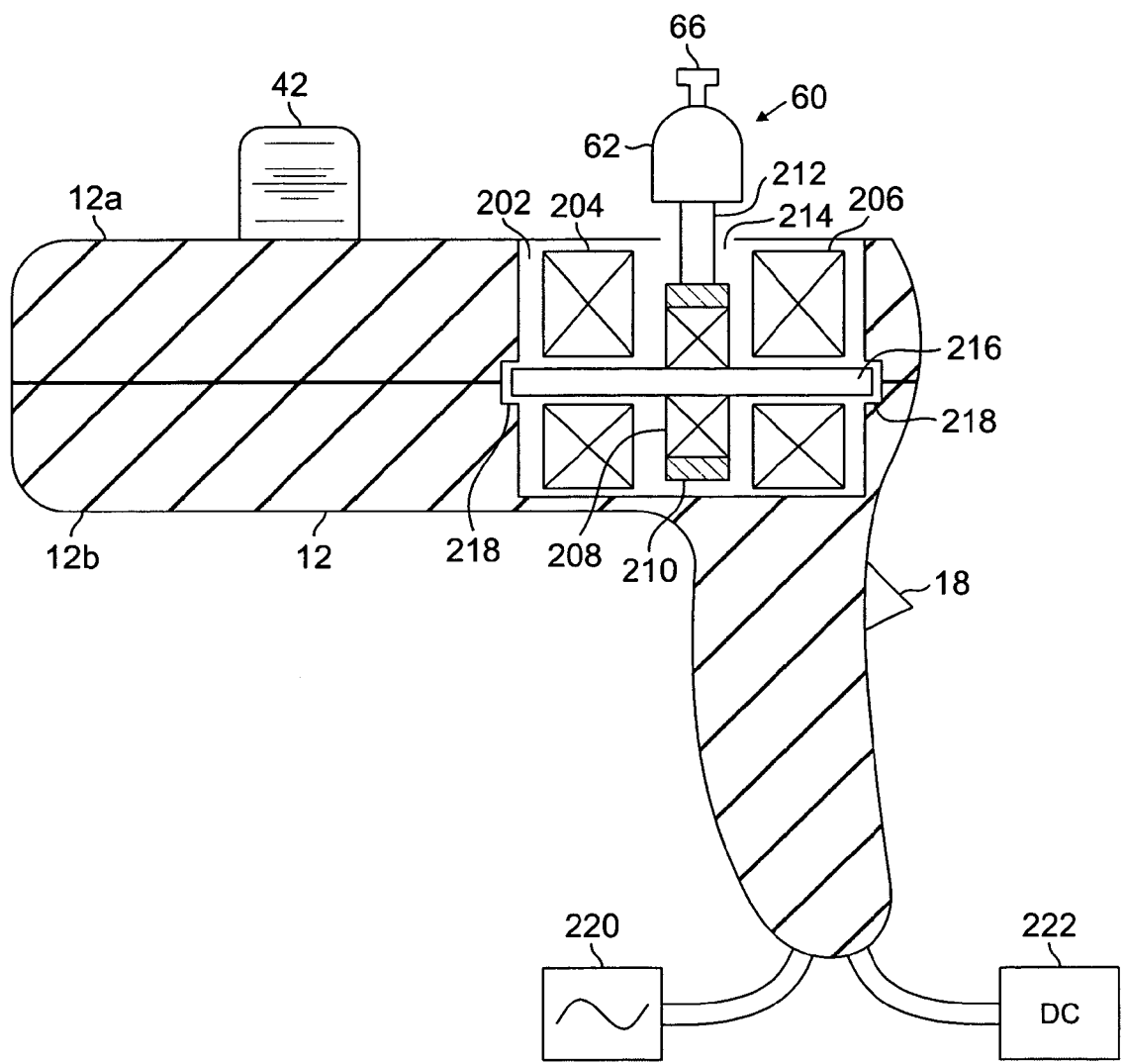
FIG. 19 is a cross-sectional view of vibration assisted needle device in accordance with another embodiment of the invention, wherein the needle support and the needle are driven electromagnetically.

FIG. 19 is a cross-sectional view of a vibration assisted biopsy needle device 200 in accordance with another embodiment of the invention, wherein the needle support 60 and the needle 14 (not shown) are driven electromagnetically. The device 200 comprises a top housing 12a and a bottom housing 12b, defining a chamber 202. First and second stationary solenoids 204, 206 are provided within the chamber 202. A third, movable solenoid 208 is provided between the first and second solenoids 204, 206. A sleeve 210 is provided over the third solenoid 208 and a tab 212 is connected to the sleeve 210. When assembled, the tab 212 extends through a slot 214 in the top portion 12a, and is connected to the needle support 60. The top view of the slot 214 is the same as the top view of the slot 15 in FIG. 3. A syringe support 42 is connected to the top housing 12a. The needle support 60 and the syringe support 42 may be the same as the supports described above. The bottom portion may include an integral handle 12c or a separate handle which is attached to the bottom portion 126. A switch 18 may be provided in the handle 12c.

A rod 216 is provided for supporting the first, second and third solenoids 204, 206, 208. The ends of the rod 216 are supported in the chamber 202 by first and second shoulders 218, respectively.

The first and second solenoids 204, 206 fit tightly over the rod so that they are stationary. The third solenoid 208 fits loosely over the rod so that it may be moved. Preferably, the outer diameter of the third solenoid 208 and the sleeve 210 are such that the sleeve does not contact the bottom of the chamber 202, to decrease friction.

A source 220 of alternating current ("AC") is provided for energizing the first and second solenoids 204, 206. A source 222 of direct current ("DC") is also provided for energizing the third solenoid 208. The switch 18 controls the application of current to the circuit comprising the first and second solenoids 204, 206 and to the third solenoid 208.

The first and second solenoids 204, 206 are polarized in opposite directions, so that when the solenoids are energized, the direction of the magnetic fields generated by the solenoids are in opposite directions. When energized, the direction of the magnetic field generated by the third moving solenoid 208 is in the same direction as one of the stationary solenoids and in the opposite direction as the other stationary solenoid. As the alternating current flows through the first and second solenoids 204, 206, the generated magnetic fields provide an attractive force on the third moving solenoid 208, toward a first one of the stationary solenoids, in this example, the first solenoid 204, and a repulsive force towards a second one of the stationary solenoids, in this example, the second solenoid 206. The third solenoid 208, the needle support 60 and hence, the needle 14, will thereby be moved toward the solenoid 204 and away from the solenoid 206. When the current is reversed, an opposite magnetic field will be generated, providing an attractive force toward the second solenoid 206 and a repulsive force toward the first solenoid 204. The moving solenoid 208, the needle support 60 and the needle 14 will thereby be moved toward the second solenoid 208. Forward and backward motion along the longitudinal axis of the needle 14 is thereby generated in accordance with the direction and slope of the alternating current. The reciprocatory motion of the needle support 60 and the needle 14 is stabilized by the slot 214, which is preferably just slightly wider than the width of the tab 212.

The first and second solenoids 204, 206 are preferably connected in parallel, to lower the inductance of the circuit. Lower inductance enables faster switching between the directions of the magnetic fields. However, the solenoids 204, 206 may be connected in series, as well.

Figure 20A:
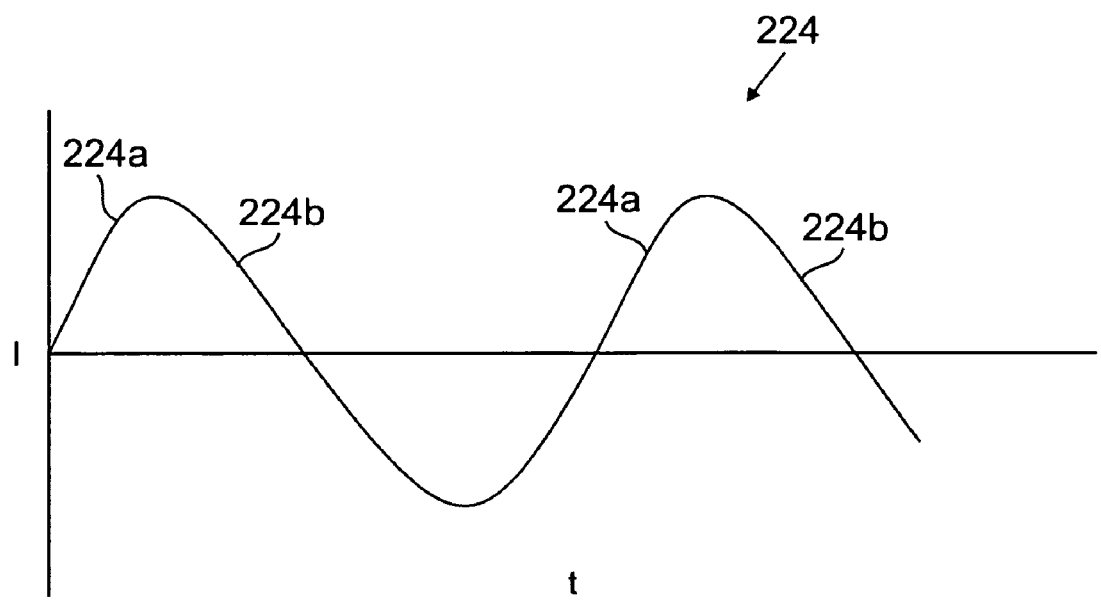
FIG. 20a and FIG. 20b are examples of waveforms for driving the needle device in the embodiment of FIG. 19.
Figure 20B:
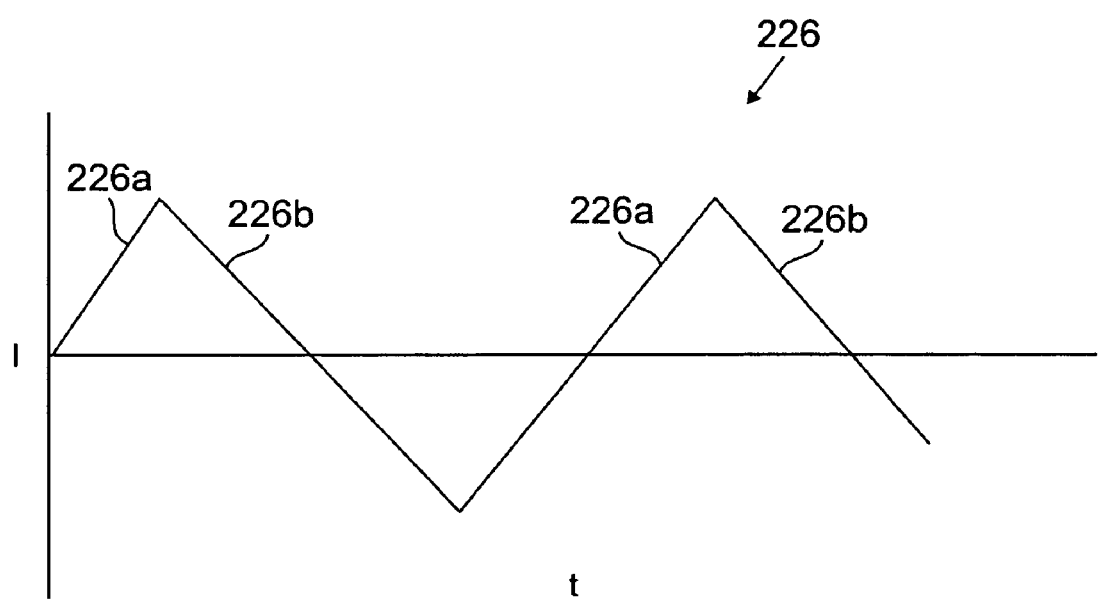

FIGS. 20a and 20b are examples of waveforms 224, 226, respectively, which can be used to drive the solenoids 204, 206. The waveforms 224, 226 preferably include a first steep portion 224a, 226a, and a second, less steep portion 224b, 226b. The solenoids 204, 206 are arranged so that the third solenoid 208 is attracted by the first solenoid 204 and repulsed by the second solenoid 206 during the steep, upwardly sloped portion 224a, 226a, of waveforms 222, 224, respectively, so that the third solenoid 208, and hence the needle 14, move rapidly forward during that time period. The third solenoid 208 is attracted towards the second solenoid 206 and repulsed by the first solenoid 206 during the less-steep portions 224b, 226b of the waveforms 224, 226, respectively, so that the third solenoid 208, and hence the needle 14, return during that time period, with less speed than the forward movement. As discussed above, more rapid forward movement than return movement, is advantageous. The needle support 60 may be reciprocated forward and backward at a rate of about 333 Hertz to about 1 Kilohertz.

The third solenoid 208, the sleeve 210, the needle support 60 and the needle 14 are the only moving components of the device 200. As in the first and second embodiments, the total mass of the reciprocating components is preferably much less (about $\frac{1}{100}$ or less) than the mass of the device 200 itself, minimizing the recoil when the needle 14 returns to its original position.

The device 200 is used to obtain a sample of a tissue of interest in the same manner as described above. As above, the vibration of the needle 14 eases the advance of the needle 14 through tissue to the site of interest, penetration of the site of interest and collection of the tissue of interest.

Alternatively, the third solenoid 222 may be stationary and the first and second solenoids 204, 206 may move. The needle support 60 would then be coupled to one of the moving solenoids 204 or 206. In addition, instead of two stationary solenoids, one stationary solenoid may be used to drive one moving solenoid 208. A resilient member, such as a spring or resilient material, such as neoprene, may also be provided between a side wall of the chamber and the moving solenoid 208, instead of the second stationary solenoid.

In another alternative, instead of stationary solenoids 204, 206, one or more stationary permanent magnets, such as ring magnets, may be used. The permanent magnets would be arranged so that the direction of the magnetic fields are in opposite directions. The moving solenoid 208 would then be energized by the alternating current, and be alternately attracted and repulsed by each of the permanent magnets.

While in the second and third embodiments, a post extends through a slot in the housing to a needle support external to the housing, the needle support may be within a chamber of the housing and the slot may be defined by an internal wall of the housing, as discussed above with respect to the first embodiment.

Those skilled in the art will understand that other changes may also be made in the embodiments described above, which do not depart from the scope of the present invention, which is defined by the claims, below.

We claim:

1. A method of conducting a needle biopsy procedure, comprising:
    mounting a biopsy needle to a needle support of a device to cause reciprocation of the biopsy needle;
    reciprocating the biopsy needle along its longitudinal axis by the device by converting rotational motion to reciprocatory motion of the needle support by coupling the needle support to a circumferential groove on an external surface of a rotatable cylinder of the device, the groove having at least a portion at an oblique angle with respect to an axis of rotation of the cylinder, the needle support being coupled to the groove through a slot in a housing, the slot having a longitudinal axis aligned with the longitudinal axis of the needle and at an oblique angle with respect to at least a portion of the groove, such that rotation of the cylinder causes reciprocation of the needle support along the longitudinal axis of the slot;
    advancing the reciprocating needle to a site of interest within a subject;
    collecting tissue at the site of interest; and
    withdrawing the needle.

2. The method of claim 1, comprising rotating the cylinder hydraulically.

3. The method of claim 1, comprising rotating the cylinder by a rotational motor.

4. A method of conducting a needle biopsy procedure, comprising:
    reciprocating a biopsy needle along a longitudinal axis of the needle, by electromagnetically generated linear motion;
    advancing the reciprocating needle to a site of interest within a subject;
    collecting tissue at the site of interest; and
    withdrawing the needle.

5. The method of claim 4, comprising reciprocating the needle by coupling the needle to a movable solenoid in a chamber of the device, energizing the solenoid and alternately attracting and repulsing the energized solenoid by a magnet in the chamber.

6. The method of claim 5, comprising alternately attracting and repulsing the movable solenoid by an energized stationary solenoid in the chamber.

7. The method of claim 6, further comprising alternately attracting and repulsing the movable solenoid by a second energized stationary solenoid, on an opposite side of the movable solenoid than the first solenoid.

8. The method of claim 5, comprising, alternately, attracting and repulsing the movable solenoid by at least one permanent magnet.

9. A method of conducting a needle biopsy procedure, comprising:
    automatically reciprocating a biopsy needle along a longitudinal axis of the needle, the needle is being connected to a syringe with a plunger;
    advancing the reciprocating needle to a site of interest within a subject;
    withdrawing the plunger to create a negative pressure in a bore of the needle, prior to collecting the tissue at the site of interest;
    collecting tissue at the site of interest;
    reciprocating the needle during tissue collection; and
    withdrawing the needle.

10. The method of claim 9, wherein the needle is connected to a pump:
the method comprising activating the pump to create a negative pressure in a bore of the needle, prior to collecting the tissue at the site of interest.

11. The method of claim 9, further comprising stopping reciprocation of the needle prior to withdrawing the plunger.

12. A method of conducting a needle biopsy procedure, comprising:
hydraulically generating rotary motion;
converting the rotary motion to reciprocating motion of a biopsy needle;
inserting the biopsy needle into a subject;
advancing the reciprocating needle toward a site of interest;
inserting the reciprocating needle into the site of interest; and
collecting tissue at the site of interest.

13. A method of conducting a needle biopsy procedure with a device comprising a housing comprising at least one wall defining a chamber and a longitudinal slot through a wall of the chamber, a needle support external to the chamber to support a needle external to the chamber, and reciprocating means within the chamber and coupled to the needle support, the method comprising:
mounting the biopsy needle to the needle support of the device;
reciprocating the needle support along the longitudinal axis of the slot by the reciprocating means to reciprocate the biopsy needle along its longitudinal axis;
advancing the reciprocating needle to a site of interest within a subject;
collecting tissue at the site of interest; and
withdrawing the needle.

14. The method of claim 13, wherein the reciprocating means comprises a bearing assembly, the method comprising:
reciprocating the needle support along the longitudinal axis of the slot by the bearing assembly, to reciprocate the needle.

15. The method of claim 13, wherein the reciprocating means comprises a ball bearing assembly, the method comprising:
reciprocating the needle support along the longitudinal axis of the slot by the ball bearing assembly, to reciprocate the needle.

16. The method of claim 13, wherein the reciprocating means comprises a grooved cylinder, the method comprising:
reciprocating the needle support along the longitudinal axis of the slot by the rotation of the grooved cylinder, to reciprocate the needle.

17. The method of claim 13, wherein the reciprocating means comprises a first electromagnet coupled to the needle support and at least one second, stationary electromagnet proximate the first electromagnet, the method comprising:
reciprocating the needle support along the longitudinal axis of the slot by selectively energizing the second electromagnet to cause reciprocation of the first electromagnet and the needle support.

18. The method of claim 13, further comprising:
coupling the needle support to the reciprocating means by a post extending through the slot, the post having a first end coupled to the reciprocating means and a second end coupled to the needle support.

19. The method of claim 13, comprising:
advancing the reciprocating needle with a stylet within a bore of the needle; and
withdrawing the stylet prior to collecting the tissue.

20. The method of claim 13, comprising reciprocating the needle prior to insertion of the needle into the subject and inserting the reciprocating needle into the subject.

21. The method of claim 13, comprising reciprocating the needle while collecting the tissue.

22. The method of claim 13, further comprising guiding the needle to the site of interest by magnetic resonance imaging.

* * * * *

UNITED STATES PATENT AND TRADEMARK OFFICE
CERTIFICATE OF CORRECTION

| | | |
|---|---|---|
| PATENT NO. | : 7,008,383 B1 | |
| APPLICATION NO. | : 10/728376 | |
| DATED | : March 7, 2006 | |
| INVENTOR(S) | : Jevan Damadian et al. | |

It is certified that error appears in the above-identified patent and that said Letters Patent is hereby corrected as shown below:

TITLE PAGE, ITEM (75): add inventor "Michael Votruba"

Signed and Sealed this

Fifth Day of September, 2006

JON W. DUDAS
*Director of the United States Patent and Trademark Office*